US009439961B2

(12) United States Patent
Shimohata et al.

(10) Patent No.: US 9,439,961 B2
(45) Date of Patent: Sep. 13, 2016

(54) PHARMACEUTICAL COMPOSITION FOR TREATING ISCHEMIC EVENTS

(71) Applicant: Niigata University, Niigata (JP)

(72) Inventors: Takayoshi Shimohata, Niigata (JP); Lawrence M. Kauvar, San Francisco, CA (US)

(73) Assignee: NIIGATA UNIVERSITY, Niigata (JP)

( * ) Notice: Subject to any disclaimer, the term of this patent is extended or adjusted under 35 U.S.C. 154(b) by 64 days.

(21) Appl. No.: 14/151,507

(22) Filed: Jan. 9, 2014

(65) Prior Publication Data

US 2014/0127233 A1 May 8, 2014

Related U.S. Application Data

(60) Division of application No. 13/359,281, filed on Jan. 26, 2012, now Pat. No. 8,652,476, which is a continuation-in-part of application No. PCT/JP2010/062631, filed on Jul. 27, 2010.

(30) Foreign Application Priority Data

| Jul. 27, 2009 | (JP) | 2009-174098 |
| Jul. 27, 2009 | (JP) | 2009-174099 |
| May 31, 2010 | (JP) | 2010-124374 |
| May 31, 2010 | (JP) | 2010-124382 |

(51) Int. Cl.
| A61K 38/37 | (2006.01) |
| A61K 38/49 | (2006.01) |
| C07D 231/12 | (2006.01) |
| C07D 233/56 | (2006.01) |
| A61K 45/06 | (2006.01) |
| A61K 39/395 | (2006.01) |
| C07K 16/22 | (2006.01) |
| A61K 38/17 | (2006.01) |
| A61K 38/18 | (2006.01) |
| A61K 31/277 | (2006.01) |
| A61K 39/00 | (2006.01) |

(52) U.S. Cl.
CPC ......... A61K 39/3955 (2013.01); A61K 31/277 (2013.01); A61K 38/177 (2013.01); A61K 38/1866 (2013.01); A61K 38/49 (2013.01); A61K 45/06 (2013.01); C07K 16/22 (2013.01); A61K 2039/505 (2013.01); A61K 2300/00 (2013.01)

(58) Field of Classification Search
CPC .. A61K 38/77; A61K 38/1866; A61K 38/49; A61K 2039/505; A61K 2300/00; A61K 45/06; A61K 31/277; A61K 38/177; A61K 31/404; C07D 231/12; C07D 233/56; C07D 233/08; C07D 413/14; C07D 403/06
USPC ....... 514/414, 235.5, 121, 7.5, 7.6; 424/158, 424/94.67, 94.64
See application file for complete search history.

(56) References Cited

U.S. PATENT DOCUMENTS

| 4,976,959 A | 12/1990 | Berger, Jr. et al. |
| 2003/0133972 A1* | 7/2003 | Danthi ................ A61K 47/488 424/450 |
| 2005/0053599 A1 | 3/2005 | Van Bruggen et al. |
| 2007/0258980 A1 | 11/2007 | Van Bruggen et al. |
| 2009/0123452 A1 | 5/2009 | Madison |

FOREIGN PATENT DOCUMENTS

| JP | 63-22026 | 1/1988 |
| JP | 11-515010 | 12/1999 |
| JP | 2002-534359 | 10/2002 |
| JP | 2006-525270 | 11/2006 |
| WO | WO-97/15323 | 5/1997 |
| WO | WO-2004/096268 | 11/2004 |
| WO | WO-2007/128526 | 11/2007 |

OTHER PUBLICATIONS

Orphanos et al., Acta Oncologica 48: 964-970, 2009.*
Almagro and Fransson, "Humanization of Antibodies" Frontiers in Bioscience (2008) 13:1619-1633.
Baeuerle et al., "Bispecific T-Cell Engaging Antibodies for Cancer Therapy" Cancer Research (2009) 69(12):4941-4944.
Bambace et al., "The effect of P2Y-mediated platelet activation on the release of VEGF and endostatin from platelets" Platelets (2010) 21(2):85-93.
Benhar, "Design of synthetic antibody libraries" Expert Opin. Biol. Ther. (2007) 7(5):763-779.
Chiba, "Effect of anti-VEGF receptor antagonist(VGA1155) after middle cerebral artery occlusion in rats" Annual Meeting of the Japan Neurosurgical Society Abstract (2007) 66:1 K-P01-1-2.
Chica et al., Curr. Opin. Biotechnol. (2005) 16(4):378-384.
Chu, "Aflibercept (AVE0005): an alternative strategy for inhibiting tumour angiogenesis by vascular endothelial growth factors" Expert Opin. Biol. Ther. (2009) 9(2):263-271.
Collarini et al., "Potent High-Affinity Antibodies for Treatment and Prophylaxis of Respiratory Syncytial Virus Derived from B Cells of Infected Patients" Journal of Immunology (2009) 183:6338-6345.
Deschacht et al., "A Novel Promiscuous Class of Camelid Single-Domain Antibody Contributes to the Antigen-Binding Repertoire" Journal of Immunology (2010) 184:5696-5704.
Fagan et al., Stroke (2004) 35:2220-2225.
Fitchett, "The impact of bleeding in patients with acute coronary syndromes: how to optimize the benefits of treatment and minimize the risk" Can. J. Cardiol. (2007) 23(8):663-671.
Guo et al., "Cell-Selex: Novel Perspectives of Aptamer-Based Therapeutics" International Journal of Molecular Sciences (2008) 9:668-678.
Holtzman et al., "Miniature protein ligands for EVH1 domains: Interplay between affinity, specificity, and cell motility" Biochemistry (2007) 46(47):13541-13553.
Jakobovits et al., "From XenoMouse technology to panitumumab, the first fully human antibody product from transgenic mice" Nature Biotechnology (2007) 25(10):1134-1143.

(Continued)

Primary Examiner — Phuong Huynh
(74) Attorney, Agent, or Firm — Morrison & Foerster LLP

(57) ABSTRACT

Methods and pharmaceutical compositions for treating severe ischemic events including cerebral infarction, cardiac infarction, or pulmonary embolism, comprising a thrombolytic intervention including thrombolytic agents and an inhibitor of vascular endothelial growth factor (VEGF) receptor-mediated signal transduction are disclosed.

4 Claims, 7 Drawing Sheets

(56) References Cited

OTHER PUBLICATIONS

Kanazawa et al., "VEGF Expression of Vascular Endothelial Cells in Middle Cerebral Artery Occlusion Rat Models" Program and Abstracts of the Meeting of the Japanese Society of Neurology (2008) 49:267.

Kimura et al., "Brain Protective Effect of VEGF-Neutralizing Antibody Against Cerebral Venous Infarction" Jomyaku (2004) 115(2):155 B-22.

Kumai et al., J. Cerebral Blood Flow & Metabolism (2007) 27:1152-1160.

Kutchukian et al., "All-Atom Model for Stabilization of α-Helical Structure in Peptides by Hydrocarbon Staples" Journal of the American Chemical Society (2009) 131:4622-4627.

Morris, "RNA-Directed Transcriptional Gene Silencing and Activation in Human Cells" Oligonucleotides (2009) 19(4):299-305.

Murray et al., "The molecular basis of thrombolysis and its clinical application in stroke" Journal of Internal Medicine (2010) 267:191-208.

Nagai et al., Circulation (1999) 100:2541-2546.

Petersson and Schepartz, "Towars β-Amino Acid Proteins: Design, Synthesis, and Characterization of a Fifteen Kilodalton β-Peptide Tetramer" Journal of the American Chemical Society (2008) 130:821-823.

Seffernick et al., J. Bacteriol. (2001) 183(8):2405-2410.

Shimohata et al., "Neuro-Vascular Protection Therapy in the Post t-PA Age" Niigata Medical Association Kaiho (2009) 706:2-6.

Siemeister et al., "An antagonistic vascular endothelial growth factor (VEGF) variant inhibits VEGF-stimulated receptor autophosphorylation and proliferation of human endothelial cells" PNAS USA (1998) 95:4625-4629.

Stancovski et al., PNAS USA (1991) 88:8691-8695.

The National Institute of Neurological Disorders and Stroke rt-PA Stroke Study Group, "Tissue Plasminogen Activator for Acute Ischemic Stroke" New England Journal of Medicine (1995) 333(24):1581-1587.

Van Regenmortel and Muller, "D-peptides as immunogens and diagnostic reagents" Current Opinion in Biotechnology (1998) 9:377-382.

Wesolowski et al., "Single domain antibodies: promising experimental and therapeutic tools in infection and immunity" Med. Microbiol. Immunol. (2009) 198(3):157-174.

Whalgren et al., Lancet (2008) 372(11-17):1303-1309.

Witkowski et al., Biochemistry (1999) 38(36):11643-11650.

Witte et al., Cancer and Metastasis Reviews (1998) 17:155-161.

Wurch et al., "Development of Novel Protein Scaffolds as Alternatives to Whole Antibodies for Imaging and Therapy: Status on Discovery Research and Clinical Validation" Current Pharmaceutical Biotechnology (2008) 9:502-509.

Xu and Qu, "Protein tyrosine phosphatases in the JAK/STAT pathway" Front. Biosci. (2008) 13:4925-4932.

Yu et al., Investigative Ophthalmology & Visual Science (2008) 49(2):522-527.

Chiba et al., "Anti-VEGF receptor antagonist (VGA1155) reduces infarction in rat permanent focal brain ischemia," Kobe J Med Sci (2008) 54(2):E136-E146.

Kimura et al., "Cerebroprotective Effects of VEGF Neutralizing Antibody on Cerebral Venous Infarction," (2004) 15(2):155(B-22) (English abstract included).

Kimura et al., "Vascular endothelial growth factor antagonist reduces brain edema formation and venous infarction," Stroke (2005) 36(6):1259-1263.

Kumai et al., "Postischemic gene transfer of soluble Flt-1 protects against brain ischemia with marked attenuation of blood-brain barrier permeability" J Cerebral Blood Flow Metab (2007) 27:1152-1160.

Minematsu, "New progress of thrombolytic therapy," Int Rev Thrombosis (2008) 3(3):262-266 (English abstract included).

Office Action in Japanese Patent Application No. JP-2010-124382, dated May 27, 2014, 9 pages (English translation included).

Office Action in Japanese Patent Application No. JP-2010-124374, dated May 27, 2014, 7 pages (English translation included).

Sato, "Anti-angiogenic drugs," Japan J Cancer Chemother (2009) 36(7):1072-1075.

Strawn et al., "Flk-1 as a target for tumor growth inhibition," Cancer Res (1996) 6(15):3540-3545.

Ueda et al., "A novel low molecular weight antagonist of vascular endothelial growth factor receptor binding: VGA1155," Mol Cancer Ther (2003) 2(11):1105-1111.

Uchiyama, "rt-PA Intraveneous Therapy," Therapeutics (2008) 42(10):1073-1081 (English abstract included).

Van Bruggen et al., "VEGF antagonism reduces edema formation and tissue damage after ischemia/reperfusion injury in the mouse brain," J Clin Invest (1999) 104(11):1613-1620.

Del Zoppo et al., "Expansion of the Time Window for Treatment of Acute Ischemic Stroke With Intravenous Tissue Plasminogen Activator," Stroke (2009) 40:2945-2948.

Hacke et al., "Thrombolysis with Alteplase 3 to 4.5 Hours after Acute Ischemic Stroke," The New England Journal of Medicine (2008) 359(13):1317-1329.

Lunsberg et al., "Efficacy and Safety of Tissue Plasminogen Activator 3 to 4.5 Hours After Acute Ischemic Stroke," Stroke (2009) 40:2438-2441.

Notice of Reasons for Rejection (translation) for JP 2015-13312, mailed Jul. 1, 2016, 6 pages.

Notice of Reasons for Rejection (translation) for JP 2015-13318, mailed Jul. 1, 2016, 8 pages.

\* cited by examiner

One hour after

Four hours after

PHARMACEUTICAL COMPOSITION FOR TREATING ISCHEMIC EVENTS

CROSS-REFERENCE TO RELATED APPLICATIONS

This application is a divisional of Ser. No. 13/359,281, filed 26 Jan. 2012, now allowed, which is a continuation-in-part of PCT/JP2010/062631, filed on 27 Jul. 2010, which claims benefit of Japanese Patent Application No. 2010-124382, filed 31 May 2010; Japanese Patent Application No. 2010-124374, filed 31 May 2010; Japanese Patent Application No. 2009-174098, filed 27 Jul. 2009; and Japanese Patent Application No. 2009-174099, filed 27 Jul. 2009. The contents of these applications are incorporated by reference herein in their entirety.

TECHNICAL FIELD

The present invention relates to methods and pharmaceutical compositions for treating ischemic events, including cerebral infarction, cardiac infarction, or pulmonary embolism employing a thrombolytic agent and an inhibitor of vascular endothelial growth factor (VEGF) receptor-mediated signal transduction.

BACKGROUND ART

Severe ischemic events including cerebral infarction, cardiac infarction, or pulmonary embolism occur as a result of local occlusion of the blood flow; i.e., ischemia. In cerebral infarction, the ischemic core at an acute stage leads irreversibly to death even though the blood flow is restored, while there is a reversible, incomplete ischemic region around the ischemic core, which is called "penumbra." The ischemic core expands unless it is treated, and the penumbra gradually disappears. As a result, the region with cerebral infarction expands pathologically, and functional disorders are caused clinically, leading to death at worst. The purpose of treatment at an acute stage of cerebral infarction is to restore the blood flow. This restoration depends on the extent and the continuation time of ischemia. That is, early recovery of cerebral infarction depends on whether the blood flow in the penumbra can be restored rapidly.

Tissue plasminogen activator (hereinafter "t-PA") is approved as a therapeutic drug for ischemic events at an acute stage, since it is effectively used for a thrombolytic therapy where an ischemia-causing thrombus is lysed to resume blood supply.

Administration of t-PA, however, is ineffective if administered after an acute stage of ischemic events. In cerebral infarction, the t-PA rather causes concomitantly occurring cerebral hemorrhage and exacerbation of prognosis. Thus, the administration of t-PA is contraindicated after an acute stage of cerebral infarction; i.e., after 3 hours or longer has passed since the onset of the cerebral infarction. In cardiac infarction, the administration of t-PA is contraindicated for patients after 6 hours or longer has passed after the onset of cardiac infarction.

Thrombolytic therapy for treating ischemic events involves a particularly high risk of cerebral hemorrhage. Any thrombolytic therapy for reducing severity of ischemic conditions has factors increasing risk, such as risk of cerebral hemorrhage (see Fitchett, D., Can. J. Cardiol. (2007) 23:663-671). This includes mechanical thrombolysis as well as biochemical thrombolysis.

Therefore, keen demand has arisen for development of a treatment that can be administered to a patient after an acute stage of severe ischemic events including cerebral infarction, cardiac infarction, or pulmonary embolism without inducing complications such as cerebral hemorrhage.

DISCLOSURE OF THE INVENTION

The present invention solves the above existing problems. The invention provides a treatment that can be administered to a patient after an acute stage of severe ischemic events including cerebral infarction, cardiac infarction, or pulmonary embolism without inducing complications such as cerebral hemorrhage.

The present inventors have found that complications such as cerebral hemorrhagic transformation and exacerbation (worsening) of prognosis as a result of administration of a thrombolytic agent such as t-PA after an acute stage of severe ischemic events are caused by vessel wall protein degradation induced by activation of signal transduction from the VEGF receptor wherein this activation arises through enhancement of VEGF expression caused by vessel recanalisation resulting from administration of the thrombolytic agent. By using the aforesaid thrombolytic agent or other thrombolytic intervention, such as mechanical thrombolysis, in combination with an inhibitor that inhibits the aforesaid VEGF receptor-mediated signal transduction, for example, an antibody or other binding agent against at least one of VEGF and VEGF receptor, the thrombolytic agent or intervention can be administered to a patient with severe ischemic events without inducing complications such as cerebral hemorrhage. The utility of thrombolysis is thus increased and the window of opportunity for administration is increased.

In one embodiment of the present invention, a pharmaceutical composition and a treatment method are provided for treating severe ischemic events including cerebral infarction, cardiac infarction, or pulmonary embolism. The treatment employs a thrombolytic agent and/or mechanical thrombolysis, and at least one inhibitor of signal transduction mediated by vascular endothelial growth factor receptor (VEGF-R). The inhibitor may inhibit the binding of VEGF to VEGF-R to inhibit signal transduction mediated by VEGF-R. The thrombolytic agent and VEGF-R signal transduction inhibitor may be in the same composition and the invention includes such compositions.

MODES OF CARRYING OUT THE INVENTION

Figure 1:
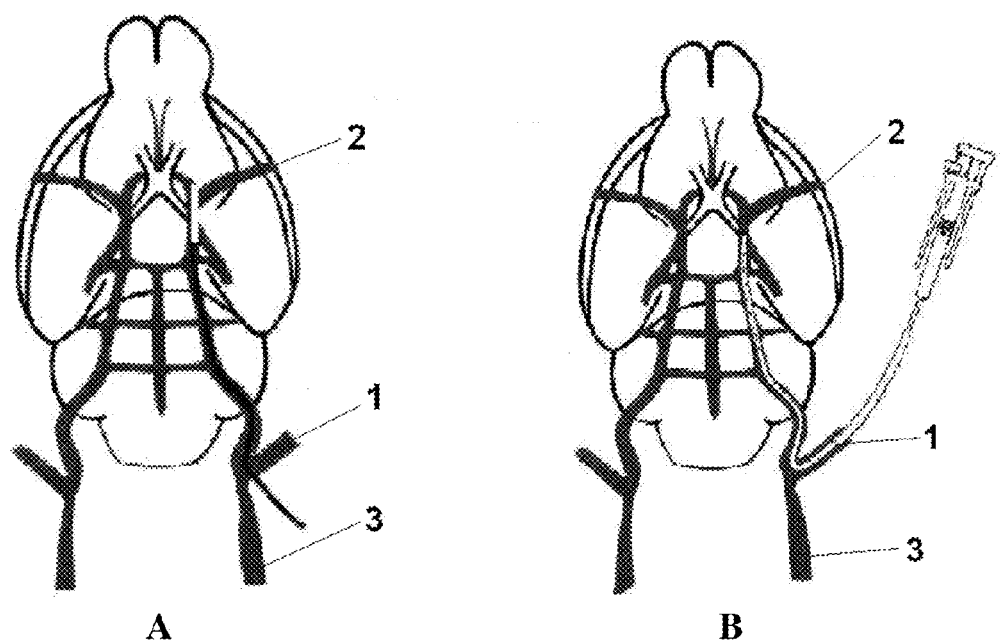
FIG. 1A is a schematic view for explaining the procedure for producing a conventional cerebral infarction rat model; (1): external carotid artery; (2) middle cerebral artery; (3) common carotid artery.
FIG. 1B is a schematic view for explaining the procedure for producing a cerebral infarction rat model in Example 1. A thrombus formed ex vivo is injected via the external carotid artery.

The pharmaceutical compositions of the present invention comprise at least a thrombolytic agent and an inhibitor of vascular endothelial growth factor receptor (VEGF-R)-mediated signal transduction. The method may employ mechanical thrombolysis instead of, or in addition to, a thrombolytic agent along with the VEGF-R signal transduction inhibitor. The compositions may contain other ingredients such as customary pharmaceutical formulation components.

The treatment of the invention may be administered to a patient at an appropriate time in relation to the "acute stage" of severe ischemic events. The "acute stage" in the present invention refers to an initial stage of the onset of severe ischemic events including cerebral infarction, cardiac infarction, or pulmonary embolism. For example, in cerebral infarction, the acute stage refers to a stage at which it is possible to attain recovery only through rapid reperfusion effected by the thrombolytic agent although cerebral nerve function disorder is caused due to reduction in the cerebral blood flow. Here, the acute stage is generally 3 hours to 6 hours of the onset of infarction. In cerebral infarction, however, the acute stage is preferably within 3 hours of the onset.

The "patient" in the present invention encompasses humans but is not limited to humans.

Thrombolytic Agents and Interventions

There is no particular restriction for the thrombolytic agent and any thrombolytic agent can be selected appropriately according to the intended purpose, so long as it can be applied to thrombolysis at an acute stage of severe ischemic events including cerebral infarction, cardiac infarction, or pulmonary embolism (hereinafter may be referred to as, for example, "ischemic disease," "ischemic symptom" or "ischemic attack"). Examples of the thrombolytic agent include tissue plasminogen activator (t-PA) or a derivative thereof, urokinase (see Murray, V., et al., *J. Intern. Med.* (2010) 267:191-208), streptokinase, single-chain urokinase-type plasminogen activator (u-PA), desmoteplase, and other proteases acting on fibrin. Other agents known to cleave fibrin are also used in the present invention. These may be used alone or in combination. Mechanical thrombolysis is also useable to treat the primary ischemic event.

In one embodiment, the thrombolytic agent comprises urokinase, tissue plasminogen activator (t-PA), or a derivative or analog thereof.

There is no particular restriction for the method for producing the thrombolytic agent and any method can be selected appropriately according to the type of the thrombolytic agent, including recombinant production and organic synthesis. Several thrombolytic agents are commercially available and any such agent is included in the scope of the invention.

There is no particular restriction for derivatives of t-PA and any derivative can be selected appropriately according to the intended purpose. Examples of derivatives of t-PA include derivatives where the t-PA is bound to a sugar chain, oligonucleotide, polynucleotide, polyethylene glycol, or other pharmaceutically acceptable additives or treating agents. Also, derivatives of t-PA may be derivatives having the same amino acid sequence of the t-PA except that one or several amino acids are substituted.

Specific examples of derivatives of t-PA include: t-PA derivatives having the same amino acid sequence of the t-PA except that part of the amino acids are substituted (e.g., derivatives known in the art, such as monteplase, pamiteplase and reteplase); and t-PA derivatives modified with a sugar chain and having the same amino acid sequence of t-PA except that part of the amino acids are substituted (e.g., tenecteplase and lanoteplase).

There is no particular restriction for the amount of the thrombolytic agent contained in the pharmaceutical composition and any amount can be selected appropriately depending on the type of the thrombolytic agent.

In addition to thrombolytic agents, mechanical methods for thrombolysis may also be employed in lieu of or in addition to such agents.

Inhibitors of Vascular Endothelial Growth Factor Receptor-Mediated Signal Transduction There is no particular restriction for the inhibitor of vascular endothelial growth factor receptor-mediated signal transduction (hereinafter referred to simply as "inhibitor") and any inhibitor can be selected appropriately according to the intended purpose. Examples of inhibitors include an inhibitor that decreases the binding of VEGF to VEGF-R, an inhibitor that inhibits the release of VEGF from platelets, an inhibitor that interacts with a component of the VEGF-R signaling pathway, an inhibitor that interacts with an enzyme that modifies a component of the VEGF-R signaling pathway, and an inhibitor that decreases the production of at least one of VEGF and VEGF receptor.

Inhibitors that Decrease the Binding of VEGF to VEGF Receptor

There is no particular restriction for the inhibitor that decreases the binding of VEGF to VEGF receptor ("binding inhibitor") and any inhibitor can be selected appropriately according to the intended purpose. Examples thereof include a specific binding partner for at least one of VEGF and VEGF-R.

Specific Binding Partners or Binding Inhibitors

There is no particular restriction for the specific binding partner (or binding inhibitor) except for an ability to inhibit the binding of VEGF and VEGF-R. Though any inhibitor can be selected appropriately according to the intended purpose, it is desirable that the binding inhibitor binds specifically to at least one of VEGF and VEGF-R. The signal transduction mediated by VEGF receptor is thus inhibited.

Examples of specific binding partners include a receptor or ligand that binds specifically to at least one of VEGF and VEGF receptor.

There is no particular restriction for the receptor or ligand and any receptor or ligand can be selected appropriately according to the intended purpose. Examples thereof include proteins such as antibodies, peptides, peptidomimetics, aptamers, carbohydrates, nucleic acids, fats, and other biological polymers.

"Antibodies" refer to generally defined antibodies and can encompass Fab fragments, single chain Fv constructs, bi-specific constructs in which one Fc is linked to two different Fab fragments, and similar constructs thereto (see Baeuerle, P. A., et al., *Cancer Res*. (2009) 69:4941-4944). To be useful, the antibodies need to be minimally antigenic in humans and thus may be human by sequence (from a transgenic animal expressing a human antibody repertoire (see Jakobovits, A., et al., *Nat. Biotechnol*. (2007) 25:1134-1143), or a recombinant library of human antibody genes (see Benhar, I., et al., *Expert Opin. Biol. Ther*. (2007) 7:763-779), may be humanized (see Almagro, J. C., et al., *Front Biosci*. (2008) 13:1619-1633) or may be isolated from a human (see Collarini, E. J., et al., *J. Immunol*. (2009) 183:6338-6345). Likewise, reduced size (low-molecular-weight) antibodies (nanobodies) such as antibodies (naturally occurring variants) found in camels (see Deschacht, N., et al., *J. Immunol*. (2010) 184:5696-5704) or sharks (see Wesolowski, J., et al., *Med Microbiol Immunol*. (2009) 198:157-174) are also useable.

Also, antibody mimics are usable and include families of proteins based on scaffolds such as: fibronectin, transferrin, glutathione transferase, lens crystallin (see Wurch, T., et al., *Curr Pharm Biotechnol*. (2008) 9:502-509). Other mimics include small peptides (see Holtzman, J. H., et al., *Biochemistry* (2007) 46:13541-13553), peptide mimics (for example, incorporating beta amino acids (see Petersson, E. J., et al., *J. Am. Chem. Soc*. (2008) 130:821-823), or D-amino acids (see Van Regenmortel, M. H., et al., *Curr Opin Biotechnol*. (1998) 9:377-382), or chemical crosslinkers to increase conformational stability (see Kutchukian, P. S., et al., *J. Am. Chem. Soc*. (2009) 131:4622-4627)), as well as non-peptide binding agents such as nucleic acid based aptamers (see Guo, K. T., et al., *Int. J. Mol. Sci*. (2008) 9:668-678).

That is, the "antibody mimic" refers to all such binding agents achieving the same functionality as an antibody, and is also usable in place of an antibody in the present invention.

For convenience in describing the disclosed invention, the present inventors focus on antibodies as a prominent embodiment of such binding agents, without limiting the scope of the present invention.

Specific Binding Partners Binding Specifically to VEGF

The designation VEGF refers to a group of glycoproteins involved with vasculogenesis and angiogenesis. When the VEGF binds as a ligand to one of the several VEGF receptor types present on vascular endothelial cells, VEGF signal transduction is activated. In severe ischemic events including cerebral infarction, cardiac infarction, or pulmonary embolism, the activation of the VEGF signal transduction promotes degradation of constituent proteins of vessel walls. For example, it was found in the present invention that cerebral bleeding concomitantly occurs in cerebral infarction.

Examples of the VEGF family include VEGF-A, VEGF-B, VEGF-C, VEGF-D, VEGF-E, placental growth factor (P1GF)-1 and P1GF-2. Each member of the VEGF family has several subtypes. For example, human VEGF-A is known to have a subtype of 121 amino acids (VEGF-$A_{121}$), a subtype of 165 amino acids (VEGF-$A_{165}$), a subtype of 189 amino acids (VEGF-$A_{189}$), a subtype of 206 amino acids (VEGF-$A_{206}$), a subtype of 145 amino acids (VEGF-$A_{145}$), and a subtype of 183 amino acids (VEGF-$A_{183}$). Also, human VEGF-B is known to have a subtype of 167 amino acids (VEGF-$B_{167}$) and a subtype of 186 amino acids (VEGF-$B_{186}$).

Specific binding partners that bind specifically to VEGF bind to any member of the VEGF family and preferentially binds several members.

There is no particular restriction for the specific binding partner that binds specifically to VEGF and any specific binding partner can be selected appropriately according to the intended purpose. Examples of the specific binding partners include polyclonal antibodies or monoclonal antibodies that recognize VEGF, antigen-binding fragments of these antibodies, chimeric antibodies or recombinant antibodies containing the antigen-binding fragments (hereinafter may be referred to as "anti-VEGF antibodies and the like"), derivatives thereof, parts of recombinants of VEGF receptors (see Chu, Q. S., *Expert Opin. Biol. Ther*. (2009) 9:263-271), and VEGF variants that bind to VEGF receptor competitively with the VEGF but do not activate the VEGF receptor (see Siemeister, G., et al., *Proc. Natl. Acad. Sci. USA* (1998) 95:4625-4629). Among them, the specific binding partner that binds specifically to the VEGF is preferably a monoclonal antibody. In one embodiment, the specific binding partner that binds specifically to the VEGF is an anti-VEGF-A neutralizing antibody, since it can efficiently inhibit the binding between VEGF receptor and VEGF-A, which is involved with breakage of blood vessels upon angiogenesis.

There is no particular restriction for the method for producing the specific binding partner that binds specifically to the VEGF and any method can be selected appropriately according to the intended purpose, such as recombinant production or organic synthesis. The specific binding partner that binds specifically to the VEGF may also be commercially available.

The specific binding partner that binds specifically to the VEGF may be, for example, the above anti-VEGF antibodies and the like themselves, their derivatives, or both of them. These antibodies or derivatives may be bound to or mixed with other ingredients such as polyethylene glycol and other pharmaceutically acceptable additives or treating agents. There is no particular restriction for the amount of the other ingredients in the specific binding partner that binds specifically to the VEGF and any amount can be selected appropriately according to the intended purpose.

Polyclonal Antibodies

The polyclonal antibody can be produced by injecting VEGF or fragments thereof as an immunogen to an animal host which is a mammal (e.g., mouse, rat, rabbit, sheep or goat) or a bird (e.g., chicken). When the immunogen is a fragment of the VEGF, there is a case where excellent immune response may be induced when the fragment is linked to a carrier protein such as bovine serum albumin or keyhole limpet hemocyanin.

The immunogen is preferably injected to the animal host according to a predetermined schedule including one or two or more booster immunizations.

The immunogen may be injected to the animal host in combination with a complete or incomplete Freund's adjuvant or other immunopotentiating agents.

The polyclonal antibody may be those purified from such antiserum through, for example, affinity chromatography using the VEGF or fragment thereof bound to an appropriate solid support, and then studied for inhibition of the binding between VEGF and VEGF receptor, and further for the fact that such inhibition of the binding therebetween can inhibit the VEGF signal transduction.

Example of the polyclonal antibody include a rabbit anti-rat VEGF antibody IgG produced using human recombinant $VEGF_{165}$ as an immunogen (RB-222, 19 kDa to 22 kDa). Notably, the RB-222 can recognize VEGF165 and VEGF121.

Monoclonal Antibodies

The monoclonal antibody may be prepared using the technique of Kohler and Milstein (*Eur. J. Immunol.* (1976) 6:511-519) or its modified technique including many techniques well known in the art. These methods involve preparation of an immortal cell line capable of producing antibodies having desired specificity.

The immortal cell line may be produced using spleen cells derived from an animal host immunized in the same manner as in the production method of the polyclonal antibody. The spleen cells are immortalized by various methods to prepare the immortal cell line having antibody producing capability.

For example, the spleen cells are immortalized by being fused with myeloma cells derived from the same animal as or different animal from the immunized animal. The fusing may be performed using various fusing techniques well known to those skilled in the art.

For example, the spleen cells and the myeloma cells are mixed with a nonionic surfactant for several minutes, and then plated at low concentration on a selection medium that enables the growth of hybrid cells but does not enable the growth of the myeloma cells. HAT (hypoxanthine, aminopterin, and thymidine) selection is employed as a preferred selection technique. In general, colonies of hybrids are observed after a sufficient time of about 1 week to about 2 weeks. A single colony is selected and cultured in a medium such as HAT (hypoxanthine, aminopterin, and thymidine-supplemented medium). The supernatant of the culture is tested for binding activity to the VEGF or fragments thereof, as well as for inhibition of the binding between VEGF and VEGF receptor, and further for whether such inhibition of the binding therebetween can inhibit the VEGF signal transduction. The hybridomas having high reactivity and specificity are preferred. Repeating cloning by the limiting dilution method selects a clone of hybridoma that stably produces a large amount of antibodies having high reactivity and specificity. The monoclonal antibody may be isolated from the supernatant of the colony of the cell line derived from growing hybridoma clone selected.

In addition, there may be used various techniques for improving yield, including intraperitoneally injecting the hybridoma cell line to an appropriate vertebrate animal host such as mouse.

The monoclonal antibody may be recovered from hybridoma cell peritoneal fluid or blood. Contaminants such as protein impurities derived from cell debris may be removed from the antibody by a conventional technique such as chromatography, gel filtration, precipitation or extraction.

Examples of the monoclonal antibody include anti-VEGF-A neutralizing antibodies of monoclonal antibody formulations such as humanized bevacizumab produced through gene recombination of mouse monoclonal antibody to the VEGF, and ranibizumab which is the Fab fragment of the bevacizumab and is gene-modified so as to be further increased in binding to the VEGF. These monoclonal antibody formulations are already applied to clinical use for malignant tumor and confirmed for safety for human.

Antigen-Binding Fragments

The antigen-binding fragment of the antibody refers to a part involving antigen binding. The antigen-binding site is formed of amino acid residues of variable (V) regions at the N-termini of a heavy (H) chain and a light (L) chain.

The antigen-binding fragment of the antibody encompasses Fab fragment and $F(ab')_2$ fragment which are obtained by degrading an intact polyclonal or monoclonal antibody with protease papain and pepsin respectively, and Fv fragment containing heterodimer of noncovalently-bonded VH and VL regions including an antigen-binding site having antigen-recognizing capability and binding ability of a native antibody molecule.

Recombinant Antibodies

The recombinant antibody may be prepared through expression cloning of an antibody gene such as transformation into an appropriate bacterial host and transfection into an appropriate mammalian host cell.

The recombinant antibody can be prepared in a large amount using a gene expression system derived from prokaryotes or eukaryotes.

Chimeric Antibodies

The chimeric antibody is a fusion protein including an antigen-binding site of the recombinant antibody and a constant domain of the same or different antibody where the antigen-binding site is supported by the constant domain so that the antigen-binding site can bind specifically to the VEGF.

The chimeric antibody contains: a short-chain variable antibody (scFv) containing an antibody heavy-chain variable region (VH) operably linked to an antibody light-chain variable region (VL); a camel heavy-chain antibody (HCAb) or a heavy-chain variable domain (VHH) of the class of light chain-free IgG produced by animals belonging to Camelidae including camel, dromedary and llama).

Derivatives

There is no particular restriction for the derivatives of the anti-VEGF antibodies and the like having inhibitory activity to the binding between VEGF and VEGF receptor and any derivative can be selected appropriately according to the intended purpose. Examples of the derivatives include derivatives where the anti-VEGF antibody is bound to a sugar chain, oligonucleotide, polynucleotide, polyethylene glycol, or other pharmaceutically acceptable additives or treating agents.

Specific examples of the derivatives of the anti-VEGF antibodies and the like include pegaptanib which is a RNA aptamer binding to exon 7 of the VEGF gene to inhibit formation of the VEGF.

The anti-VEGF antibodies and the like may be mixed with a sugar chain, oligonucleotide, polynucleotide, polyethylene glycol, or other pharmaceutically acceptable additives or treating agents.

These sugar chain, oligonucleotide, polynucleotide, polyethylene glycol, and other pharmaceutically acceptable additives or treating agents are not particularly limited and may be appropriately selected according to the intended purpose.

Specific Binding Partners that Bind Specifically to VEGF Receptor

The VEGF receptor (VEGFR) is a receptor tyrosine kinase, and is involved with expression of actions caused by the ligand VEGF, such as promotion of growth or migration of vascular endothelial cells.

Examples of the VEGF receptor known include VEGFR-1 (hereinafter may be referred to as "Flt-1"), VEGFR-2 (KDR, hereinafter may be referred to as "Flk-1"), VEGFR-3 (hereinafter may be referred to as "Flt-4"), soluble VEGFR-1, soluble VEGFR-2, and soluble VEGFR-3. Each member of the VEGF family binds to a predetermined receptor(s): VEGF-A binds to VEGFR-1 and VEGFR-2; VEGF-B, P1GF-1 and P1GF-2 each bind to VEGFR-1; VEGF-C and VEGF-D each bind to VEGFR-2 and VEGFR-3; and VEGF-E binds to VEGFR-2.

The specific binding partner that binds specifically to the VEGF receptor may bind to any of the above VEGF receptors.

There is no particular restriction for the specific binding partner that binds specifically to the VEGF receptor and any specific binding partner can be selected appropriately according to the intended purpose. The specific binding partner that binds specifically to the VEGF receptor may be selected from the group consisting of analogs of the VEGF, competitive inhibitors of the VEGF, polyclonal antibodies or monoclonal antibodies or aptamers recognizing the VEGF receptor, antibodies that antagonize the VEGF receptor to the VEGF, antibodies that binds specifically to the VEGF receptor to remove the VEGF from blood, antigen-binding fragments of these antibodies, chimeric antibodies or recombinant antibodies containing the antigen-binding fragments (hereinafter may be referred to as "anti-VEGFR antibodies and the like"), derivatives thereof, VEGF receptor peptides or small molecule mimics of the VEGF receptor peptides that bind to the VEGF receptor but do not activate the VEGF receptor, and VEGF receptor peptides or small molecule mimics of the VEGF receptor peptides that reduce the effective level of VEGF available for stimulating the VEGF receptor. Among them, the specific binding partner that binds specifically to the VEGF receptor is preferably monoclonal antibodies, more preferably anti-VEGFR-1 neutralizing antibodies and anti-VEGFR-2 antibodies.

Here, the "small molecule mimics of the VEGF peptides" refer to molecules that are smaller than a peptide of the VEGF in the complete form and that exhibit the same functions as the VEGF peptide.

Also, the "small molecule mimics of the VEGF receptor peptides" refer to molecules that are smaller than a peptide of the VEGF receptor in the complete form and that exhibit the same functions as the VEGF receptor peptide.

There is no particular restriction for the method for producing the specific binding partner that binds specifically to the VEGF receptor and any method can be selected according to the intended purpose. Examples of the method include a gene recombination method and a synthesis method. The specific binding partner that binds specifically to the VEGF receptor may also be a commercially available one.

The specific binding partner that binds specifically to the VEGF may be the above anti-VEGFR antibodies and the like themselves, their derivatives themselves, or both of them. These antibodies or derivatives may be bound to or mixed with other ingredients such as polyethylene glycol and other pharmaceutically acceptable additives or treating agents. There is no particular restriction for the amount of the other ingredients in the specific binding partner that binds specifically to the VEGF receptor and any amount can be selected appropriately according to the intended purpose.

Polyclonal Antibodies, Monoclonal Antibodies, and Antigen-Binding Fragments

The polyclonal antibodies, monoclonal antibodies, and antigen-binding fragments can be produced using as an immunogen the VEGF receptor or fragments thereof by the same method as the above method for producing the polyclonal antibody, monoclonal antibody, and antigen-binding fragment recognizing the VEGF.

Recombinant Antibodies

The recombinant antibody can be produced by the same method as the above method for producing the recombinant antibody recognizing the VEGF.

Chimeric Antibodies

Examples of the chimeric antibody include antibodies that are the same as the chimeric antibodies recognizing the VEGF except that these antibodies are a fusion protein including an antigen-binding site of the recombinant antibody and a constant domain of the same or different antibody where the antigen-binding site is supported by the constant domain so that the antigen-binding site can bind specifically to the VEGF receptor.

Derivatives

There is no particular restriction for the derivatives of the anti-VEGFR antibodies and the like having inhibitory activity to the binding between VEGF and VEGF receptor and any derivative can be selected appropriately according to the intended purpose. Examples of the derivatives include derivatives where the anti-VEGFR antibodies and the like are bound to a sugar chain, oligonucleotide, polynucleotide, polyethylene glycol, or other pharmaceutically acceptable additives or treating agents.

The anti-VEGFR antibodies and the like may be mixed with a sugar chain, oligonucleotide, polynucleotide, polyethylene glycol, or other pharmaceutically acceptable additives or treating agents.

Examples of the additives, treating agents, oligonucleotide, polynucleotide, or polyethylene glycol include the same as used in the anti-VEGF antibodies and the like.

These sugar chain, oligonucleotide, polynucleotide, polyethylene glycol, and other pharmaceutically acceptable additives or treating agents are not particularly limited and may be appropriately selected according to the intended purpose.

Inhibitors that Inhibit the Release of VEGF from Platelets

There is no particular restriction for inhibitors that inhibit the release of VEGF from platelets and any inhibitor can be selected appropriately according to the intended purpose. Examples thereof include inhibitors that decrease the binding of adenosine diphosphate (ADP) to the ADP receptor on platelets (see Bambace, N. M., et al., *Platelets* (2010) 21:85-93).

There is no particular restriction for the inhibitors that decrease the binding of ADP to ADP receptor and any inhibitor can be selected appropriately according to the intended purpose. Examples thereof include specific binding partners for at least one of ADP and ADP receptor (hereinafter may be referred to as "binding inhibitor" that inhibits the binding of ADP to ADP receptor).

There is no particular restriction for the above specific binding partner and any specific binding partner can be selected appropriately according to the intended purpose, so long as it can bind specifically to at least one of ADP and ADP receptor to inhibit the binding between ADP and ADP receptor. Examples thereof include competitive inhibitors of ADP receptors, polyclonal antibodies or monoclonal antibodies or aptamers that recognize ADP or ADP receptor, ADP peptides or small molecule mimics of the ADP peptides that bind to the ADP receptor but do not activate the ADP receptor, and ADP receptor peptides or small molecule mimics of the ADP receptor peptides that bind to ADP.

Here, the "small molecule mimics of the ADP peptides" refer to molecules that are smaller than a peptide of the ADP in the complete form and that exhibit the same functions as the ADP peptide.

Also, the "small molecule mimics of the ADP receptor peptides" refer to molecules that are smaller than a peptide of the ADP receptor in the complete form and that exhibit the same functions as the ADP receptor peptide.

Inhibitors that Interact with a Component of the VEGF-R Signaling Pathway, and Inhibitors Interacting with an Enzyme that Modifies a Component of the VEGF-R Signaling Pathway At least one of the inhibitor that interacts with a component of the VEGF-R signaling pathway, and the inhibitor that interacts with an enzyme that modifies a component of the VEGF-R signaling pathway (hereinafter may be referred to as "VEGF receptor signaling pathway inhibitor") may be any inhibitor of VEGF R-mediated signal transduction, so long as it can prevent hemorrhage caused by administering t-PA to a patient after an acute stage of severe ischemic events including cerebral infarction, cardiac infarction, or pulmonary embolism.

There is no particular restriction for the component of the VEGF-R signaling pathway and any component can be selected appropriately according to the intended purpose. Examples thereof include phospholipase (PLCγ), protein kinase C (PKC), Raf, MAP kinase kinase (MEK), extracellular signal-regulated kinase (ERK), PI3 kinase (PI3K), pyruvate dehydrogenase kinase (PDK1), and Akt.

There is no particular restriction for the enzyme that modifies the component of the VEGF-R signaling pathway and any enzyme can be selected appropriately according to the intended purpose. Examples thereof include PLCγ inhibitory enzyme, PKC inhibitory enzyme, Raf inhibitory enzyme, MEK inhibitory enzyme, ERK inhibitory enzyme, PI3K inhibitory enzyme, PDK1 inhibitory enzyme and Akt inhibitory enzyme.

The VEGF-R signaling pathway inhibitor may also be, for example, inhibitors that inhibit functions of other biomolecules, such as inhibitors that inhibit receptor kinase and other enzymatic activities, so long as their side effects are acceptable for the treatment of patients causing ischemic events.

Specific examples of the VEGF receptor signaling pathway inhibitor include SU1498 ((E)-3-(3,5-diisopropyl-4-hydroxyphenyl)-2-((3-phenyl-n-propyl)amino-carbonyl) acrylonitrile), SU5614 (5-chloro-3-((3,5-dimethylpyrrol-2-yl)methylene)-2-indolinone), SU11248 (N-(2-(diethylamino)ethyl)-5-((Z)-(5-fluoro-1,2-dihydro-2-oxo-3H-indol-3-ylidine)methyl)-2,4-dimethyl-1H-pyrrole-3-carboxamide), AZD2171 (4-((4-fluoro-2-methyl-1H-indol-5-yl)oxy)-6-methoxy-7-(3-(pyrrolidin-1-yl)propoxy) quinazoline), PTK787/ZK222584 (N-(4-chlorophenyl)-4-(pyridin-4-ylmethyl)phthalazin-1-amine succinate), sorafenib(4-(4-((4-chloro-3-(trifluoromethyl)phenyl)carbamoylamino)phenoxy)-N-methyl-pyridine-2-carboxamide), GW786034B (5-(4-(2,3-dimethyl-2H-indazol-6-yl) methylamino)-2-pyrimidinyl)amino)-2-methyl-monohydrochloride), CBO-P11 (cyclic(D-F-PQIMRIKPHQGQHIGE); Cyclo-VEGI; D-Phe-Pro (79-93), cyclic peptide having the 79th to 93rd amino acid sequence of VEGF-A), Je-11 ((RTELNVGIDFNWEYPAS)$_2$ K—NH$_2$, peptide dimer derived from immunoglobulin-like domain corresponding to the 247th to 261st amino acid sequence of VEGF-2), V1 (ATWLPPR, peptide having 8 amino acids binding to VEGFR-2), VEGFR-2 kinase inhibitor I ((Z)-3-((2,4-dimethyl-3-(ethoxycarbonyl)pyrrol-5-yl) methylidenyl)indolin-2-one), VEGFR-2 kinase inhibitor II ((Z)-5-bromo-3-(4,5,6,7-tetrahydro-1H-indol-2-ylmethylene)-1,3-dihydroindol-2-one), VEGFR-2 kinase inhibitor III or SU5416 (3-((2,4-dimethylpyrrol-5-yl)methylidene)-indolin-2-one), VEGFR-2 kinase inhibitor IV (3-(3-thienyl)-6-(4-methoxyphenyl)pyrazolo(1,5-a)pyrimidine), VEGFR-2/3 tyrosin kinase inhibitor (3-(indole-3-yl)-4-(3,4,5-trimethoxyphenyl)-1H-pyrrole-2,5-dione), and GW654652 (N$^2$-(5-(ethylsulphonyl)-2-methoxyphenyl)-N4-methyl-N4-(3-methyl-1H-indazol-6-yl)pyrimidine-2,4-diamine). In addition, agonists of tyrosine phosphatase can reduce signal transduction via VEGF receptor-type tyrosine kinase (see Xu, D., et al., *Front. Biosci.* (2008) 13:4925-4932). These may be used alone or in combination.

Among them, the VEGF-R signaling pathway inhibitor is preferably VEGFR-2 kinase inhibitory drugs such as SU1498, SU5416, SU11248, AZD2171, PTK787/ ZK222584, sorafenib and GW786034B, since these drugs do not adversely affect VEGFR-1 positive cells known to be involved with angiogenesis in the bone marrow.

Specific examples of the VEGFR-2 kinase inhibitory drugs include cediranib (AZD2171), sunitinib (SU11248), vatalanib (PTK787/ZK222584), sorafenib, and pazopanib (GW786034B).

Inhibitors that Decrease the Production of at Least One of VEGF and VEGF-R

There is no particular restriction for the inhibitor that decreases the production of at least one of VEGF and VEGF-R and any inhibitor can be selected appropriately according to the intended purpose. Examples thereof include an antisense nucleic acid, a small interfering RNA (siRNA) (see Morris, K. V., *Oligonucleotides* (2009) 19:299-306), and a ribozyme (see Franzen, S., et al., *Curr. Opin. Mol. Ther.* (2010) 12:223-232). These may be used alone or in combination.

These inhibitors can decrease the production of at least one of VEGF and VEGF-R by inhibiting the transcription or translation of VEGF.

Also, the pharmaceutical composition may contain separately the thrombolytic agent and the inhibitor of VEGF R-mediated signal transduction as described above, but may also be a single factor having both the thrombolytic effect and the inhibitory effect of the VEGF R-mediated signal transduction.

Such a factor can be produced, for example, in the form of a bi-specific antibody (fusion protein) having an Fab serving as the thrombolytic agent (Siller-Matula, J. M., et al., *Br. J. Pharmacol.* (2010) 159:502-517, Epub 2009 Dec. 24) and an Fab serving as the inhibitor. This bi-specific antibody can simultaneously have two different functions in the form of a single factor since the Fab serving as the thrombolytic agent acts on von Willebrand factor (vWF) and the Fab serving as the inhibitor acts on VEGF or VEGF-R. Alternatively, the thrombolytic agent and the inhibitor may be in the form of a fusion protein where they are linked directly to each other (Baeuerle, P. A., et al., *Curr. Opin. Mol. Ther.* (2009) 11:22-30).

Notably, the von Willebrand factor refers to a polymeric glycoprotein which is produced by vascular endothelial cells and megakaryocytes and exists in plasma, vascular endothelial tissue and platelets.

There is no particular restriction for the amount of the inhibitor contained in the pharmaceutical composition and any amount can be selected appropriately depending on the type of the inhibitor.

Pharmaceutical Compositions

The pharmaceutical compositions of the invention contain at least one thrombolytic agent and at least one inhibitor of VEGF-R signal transduction. These compositions may also contain other ingredients and any ingredient can be selected appropriately from pharmacologically acceptable carriers depending on, for example, the administration method or dosage form employed. Compositions useful in the invention may include only one or more inhibitors of VEGF-R signal transduction if mechanical thrombolysis is employed in place of a thrombolytic agent or if the thrombolytic agent is otherwise separately administered.

When a pharmaceutical composition is used as an oral solid preparation, examples of the other ingredients include excipients such as lactose, sucrose, sodium chloride, glucose, starch, calcium carbonate, kaolin, microcrystalline cellulose and silicic acid; integrating agents such as water, ethanol, propanol, simple syrup, glucose liquid, starch liquid, gelatin liquid, carboxymethyl cellulose, hydroxypropyl cellulose, hydroxypropyl starch, methyl cellulose, ethyl cellulose, shellac, calcium phosphate and polyvinylpyrrolidone; disintegrating agents such as dry starch, sodium alginate, agar powder, sodium hydrogen carbonate, calcium carbonate, sodium lauryl sulfate, monoglyceride stearate and lactose; lubricating agents such as purified talc, stearic acid salts, borax and polyethylene glycol; coloring agents such as titanium oxide and iron oxide; and sweetening/flavoring agents such as sucrose, bitter orange peel, citric acid and tartaric acid.

When a pharmaceutical composition is used as an oral liquid preparation, examples of the other ingredients include sweetening/flavoring agents such as sucrose, bitter orange peel, citric acid and tartaric acid; buffers such as sodium citrate; and stabilizers such as tragacanth, gum Arabic and gelatin.

When a pharmaceutical composition is used as an injection, examples of the other ingredients include pH adjusters and buffers such as sodium citrate, sodium acetate and sodium phosphate; stabilizers such as sodium pyrosulfite, EDTA, thioglycolic acid and thiolactic acid; tonicity agents such as sodium chloride and glucose; topical anesthetics such as procaine hydrochloride and lidocaine hydrochloride; and surfactants such as dimethylsulfoxide (DMSO) and polyethylene glycol.

A pharmaceutical composition may further contain, for example, a sugar chain, oligonucleotide and polynucleotide. There is no particular restriction for these sugar chain, oligonucleotide, polynucleotide, polyethylene glycol, additives and treating agents and they can be selected appropriately according to the intended purpose.

There is no particular restriction for the amount of the other ingredients in a pharmaceutical composition useful in the invention and any amount can be selected appropriately according to the intended purpose.

Administration

There is no particular restriction for the timing of administration of the components of the invention method and timing can be selected according to the intended purpose. The method is performed preferably after 3 hours of the onset of severe ischemic events including cerebral infarction, cardiac infarction, or pulmonary embolism, more preferably 3 hours to 6 hours. The method may be administered to a patient after an acute stage of ischemic events, and can advantageously improve exacerbation of prognosis and complications such as cerebral hemorrhage caused by administration of the thrombolytic agent.

There is no particular restriction for the administration method of a pharmaceutical compositions of the invention and any method can be selected appropriately according to, for example, the type or amount of the thrombolytic agent and/or the inhibitor in the pharmaceutical composition. Examples of administration method include oral administration, injection and inhalation.

There is no particular restriction for the administration dose of the pharmaceutical composition and any administration dose can be selected appropriately considering various factors of a subject to be administered, such as the age, body weight, constitution, symptom and the presence or absence of administration of a drug containing other active ingredients.

There is no particular restriction for the animal species serving as the subject to be administered and any animal species may be selected appropriately according to the intended purpose. Examples of the animal species include human, monkey, pig, bovine, sheep, goat, dog, cat, mouse, rat and bird. Among them, the pharmaceutical composition is suitably administered to human.

The thrombolytic agent and the inhibitor in pharmaceutical compositions may be administered at the same time in combination, or may be administered separately from each other. The thrombolytic agent and the inhibitor may be in the form of the same composition; or the inhibitor may be administered prior to administration of the thrombolytic agent, or the thrombolytic agent may be administered within 30 min after the administration of the inhibitor. Similar considerations apply when the thrombolysis is supplied by mechanical intervention.

When the thrombolytic agent is t-PA, the t-PA activates plasmin and the activated plasmin involves processing of the VEGF. Thus, when delivered prior to administration of the t-PA to sites where ischemic events occur such as the brain, the inhibitor binds to the VEGF or the VEGF receptor thereby removing the VEGF or the VEGF receptor from the sites where ischemic events occur such as the cerebral circulatory system, leading to stronger inhibition of the signal transduction by the VEGF. Therefore, in one embodiment, t-PA is administered after the administration of the inhibitor, or the t-PA or within 30 min after the administration of the inhibitor.

There is no particular restriction for the administration dose and the administration method of the thrombolytic agent, and any administration dose and administration method can be selected appropriately according to the intended purpose. They are preferably an administration dose and an administration method per instructions of each medical drug manufacturer.

For example, when the thrombolytic agent is alteplase, i.e., one of the t-PA drugs, there is no particular restriction for the administration dose and the administration method thereof, and any administration dose and administration method can be selected appropriately according to the intended purpose. In one exemplary method, the alteplase is intravenously administered at an administration dose of 0.6 mg/kg to 0.9 mg/kg with the upper limit being 60 mg to 90 mg per individual. Specifically, 10% of the total administration dose is bolus administered for 1 min to 2 min, and the remaining 90% is intravenously injected through drip infusion for 1 hour.

There is no particular restriction for the administration dose and the administration method of the inhibitor, and any administration dose and administration method can be selected appropriately according to the intended purpose. They are preferably an administration dose and an administration method per instructions of each medical drug manufacturer.

For example, when the inhibitor is the anti-VEGF-A neutralizing antibody or a derivative thereof, in one embodiment the anti-VEGF-A neutralizing antibody or a derivative thereof is intravenously administered at an administration dose of 5 mg/kg to 10 mg/kg.

Also, when the anti-VEGF-A neutralizing antibody is bevacizumab, in one embodiment bevacizumab in an amount of 5 mg/kg to 10 mg/kg is dissolved in 100 mL of physiological saline and the resultant solution is intravenously administered for 90 min When the inhibitor is cediranib, in one embodiment the cediranib is orally administered at a daily dose of 10 mg to 45 mg per individual, for example.

When the inhibitor is sunitinib, in one embodiment the sunitinib is orally administered once a day at a dose of 25 mg to 75 mg per individual, for example.

When the inhibitor is sorafenib, there is no particular restriction for the administration dose and the administration method of the sorafenib and any administration dose and administration method can be selected appropriately according to the intended purpose. In one embodiment, the sorafenib is orally administered once a day at a dose of 400 mg to 800 mg per individual, for example.

When the inhibitor is vatalanib, there is no particular restriction for the administration dose and the administration method of the vatalanib and any administration dose and administration method can be selected appropriately according to the intended purpose. In one embodiment, the vatalanib is orally administered once a day at a dose of 500 mg to 1,500 mg per individual, for example.

When the inhibitor is pazopanib, there is no particular restriction for the administration dose and the administration method of the pazopanib and any administration dose and administration method can be selected appropriately according to the intended purpose. In one embodiment, the pazopanib is orally administered once a day at a dose of 400 mg to 1,200 mg per individual, for example.

When the thrombolytic agent and the inhibitor in the pharmaceutical composition are administered at the same time, there is no particular restriction for the administration dose and the administration method of the pharmaceutical composition and any administration dose and administration method can be selected appropriately according to, for example, the type or amount of the thrombolytic agent and the inhibitor in the pharmaceutical composition.

Application

The pharmaceutical composition may be administered to a patient after an acute stage of ischemic events including cerebral infarction, cardiac infarction, or pulmonary embolism, and can advantageously improve exacerbation of prognosis and complications such as cerebral hemorrhage. Thus, the method and compositions can suitably be used for the treatment of severe ischemic events including cerebral infarction, cardiac infarction, or pulmonary embolism.

In the treatment of the severe ischemic events, there is preferably used a treatment method including: a step of administering the thrombolytic agent; and a step of administering the inhibitor of VEGF R-mediated signal transduction at the same time as or prior to the step of administering the thrombolytic agent.

Moreover, a kit including the thrombolytic agent and the inhibitor is encompassed by the present invention. There is no particular restriction for the concentrations of the thrombolytic agent and the inhibitor in the kit, and any concentration can be selected appropriately according to the intended purpose. Preferably, these concentrations are respectively desired amounts used for administration. The inhibitor in the kit may be an inhibitor that inhibits signal transduction caused by the binding of the VEGF to the VEGF receptor, or may be an antibody that inhibits the binding between the VEGF and the VEGF receptor, or other binding factors.

EXAMPLES

The present invention will next be described in detail by way of examples, which should not be construed as limiting the present invention. The following examples were conducted after approval of the Animal Experiments Ethical Committee of Niigata University.

Example 1

Production of Cerebral Infarction Rat Model

Experimental Animal

Sprague-Dawley rats (male, 8 weeks old, obtained from Charles River Laboratories Japan, Inc.) were used to produce cerebral infarction rat models.

Production of Cerebral Infarction Rat Model

Referring to FIGS. 1A and 1B, next will be described a method for producing cerebral infarction rat models in the present invention.

In conventional middle cerebral artery occlusion models, the middle cerebral artery was occluded by passing a nylon thread to the base portion of the middle cerebral artery (MCA) (2) from the external carotid artery (ECA) 1 or the branched portion between the external carotid artery (ECA) 1 and the common carotid artery (CCA) 3 (FIG. 1A).

In the present examples, a cerebral infarction rat model shown in FIG. 1B was produced in order to realize a state where cerebral hemorrhage concomitantly occurs as a result of administration of a thrombolytic agent after the therapeutic time window of the thrombolytic therapy. A thrombus was formed by coagulating rat's autologous blood and thrombin as a gel in a polyethylene tube catheter having a diameter of 0.35 mm (PE-50, product of Becton, Dickinson and Company). The formed thrombus was left to stand overnight and then cut to have a length of 1 mm Using the catheter, the thrombus was injected from the external carotid artery (ECA) 1 to the middle cerebral artery (MCA) 2 of the rat under anesthesia with halothane at 1% by mass to 1.5% by mass. Thereafter, the thus-treated rat was measured for cerebral blood flow (CBF) using a laser Doppler flowmetry (AFL21, product of ADVANCE Co., Ltd., Tokyo) before and 30 min or 24 hours after injection of the thrombus. Regarding the CBF measured by the laser Doppler flowmetry, the animals exhibiting such a CBF that was lower than 50% of the CBF measured before injection of the thrombus were used as cerebral infarction rat models in the following experiments.

Thrombolytic Therapy

In the thrombolytic therapy for the cerebral infarction rat models, t-PA serving as a thrombolytic agent (alteplase, product of Mitsubishi Tanabe Pharma Corporation) was injected for 30 min to the femoral vein of each cerebral infarction rat model 1 hour or 4 hours after the injection of the thrombus (10 mg/kg, 10% bolus administration and 90% drip infusion).

TTC Staining

Twenty-four hours after the injection of the thrombus, halothane was excessively administered to the rats for euthanasia which were then perfused with PBS, to thereby prepare an unfixed cerebral coronal section.

The cerebral coronal section was stained with TTC at 37° C. for 15 min in PBS (pH 7.4) containing a triphenyltetrazolium salt (TTC) at 2% by mass, and then scanned with a scanner (CanoScan™, product of Canon Co.).

The cerebral infarction and the volume of edema were calculated according to Swanson, R. A., et al. (J. Cereb. Blood Flow Metab. (1990) 10:290-293).

Results

Figure 2A:
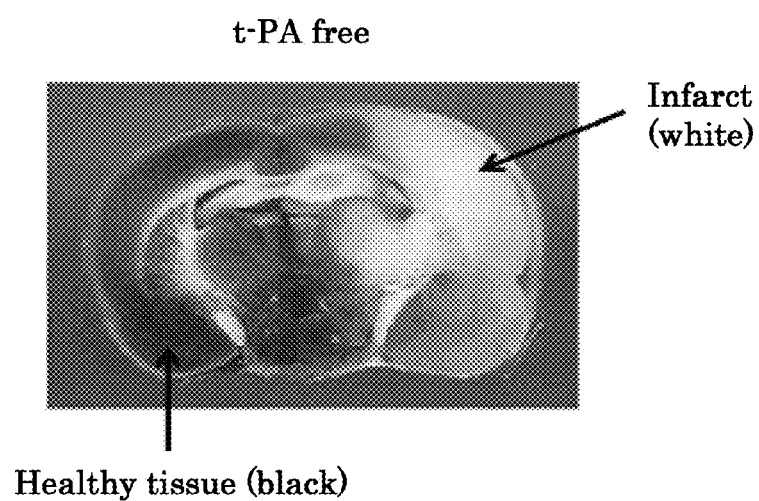
FIG. 2A is a photograph of a cerebral coronal section of an animal 24 hours after the onset of cerebral infarction induced by injection of a thrombus.
Figure 2B:
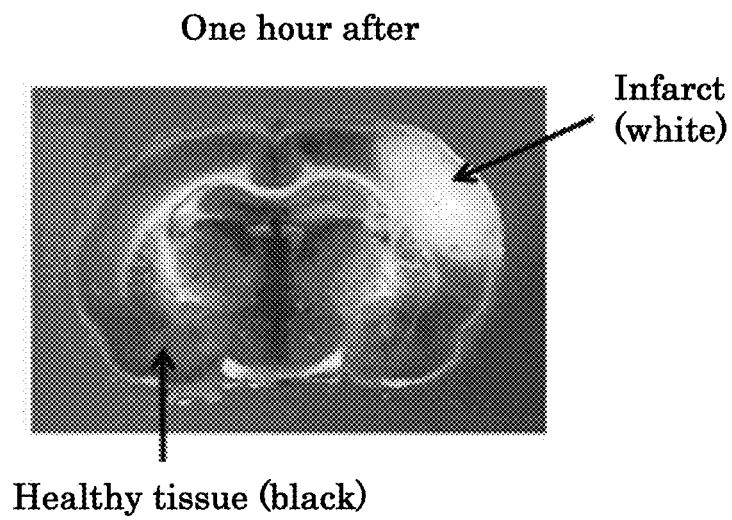
FIG. 2B is a photograph of a cerebral coronal section of an animal that receives t-PA one hour after the onset of cerebral infarction induced by injection of a thrombus.
Figure 2C:
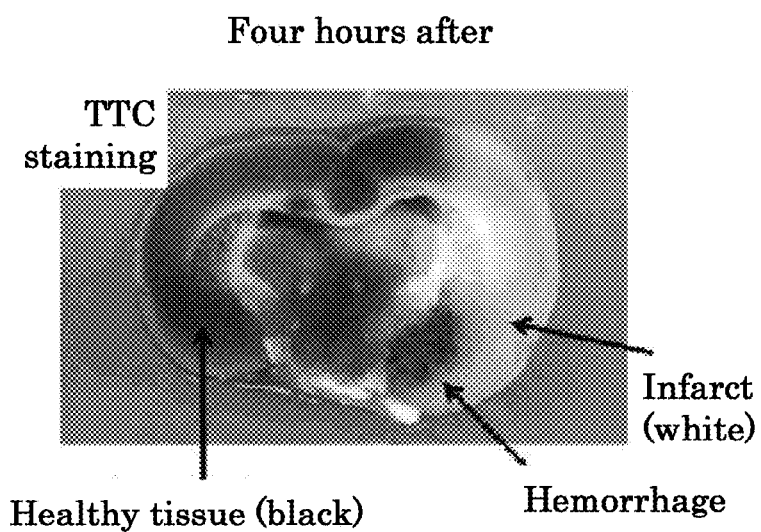
FIG. 2C is a photograph of a cerebral coronal section of an animal that receives t-PA four hours after the onset of cerebral infarction induced by injection of a thrombus, demonstrating the phenomenon of hemorrhagic transformation (widening of the zone of tissue damage).

FIGS. 2A to 2C are photographs of the cerebral coronal section in which the t-PA exhibits the effect of reducing cerebral infarction and the effect of causing cerebral hemorrhage. In each figure, the black portion indicates a healthy tissue and the white portion indicates a portion where cerebral infarction occurs.

After 24 hours had passed from the injection of the thrombus without administering the t-PA, the onset of cerebral infarction was observed in a wide range of the cerebrum at the side where the above treatment had been performed (FIG. 2A).

When the t-PA was administered one hour after the injection of the thrombus, the area where cerebral infarction occurred was found to be smaller than that in the animal receiving no t-PA (FIG. 2B).

However, when the t-PA was administered four hours after the injection of the thrombus, enlargement of the area where cerebral infarction occurred and hemorrhage in this area were considerably observed, as compared with the animal receiving the t-PA one hour after the injection of the thrombus (FIG. 2C).

From the above results, it was found that the cerebral infarction rat model can realize a state of concomitantly occurring cerebral hemorrhage and cerebral infarction exacerbation accompanied with the administration of the t-PA after an acute stage of cerebral infarction in human.

Example 2

Suppression of VEGF Using Anti-VEGF Antibody

In order to suppress or reduce concomitantly occurring cerebral hemorrhage and cerebral infarction exacerbation accompanied with the administration of the t-PA after an acute stage of cerebral infarction in human, 100 µg of rabbit anti-rat VEGF antibody IgG (RB-222, product of Lab Vision-NeoMarkers, hereinafter "anti-VEGF antibody") was bolus administered together with the t-PA. In the control experiment, 100 µg of rabbit anti-human IgG (R5G10-048, product of OEM Concepts, hereinafter "control antibody") was bolus administered together with the t-PA.

Western Blotting

Using the total cell extract as a sample, western blotting was performed according to the method described in Shimohata, T., et al. (J. Cereb. Blood Flow Metab. (2007) 27:1463-1475).

The VEGF was detected using anti-VEGF antibody (SC-152, product of Santa Cruz Biotechnologies, dilution ratio: 1:200) as a primary antibody, and peroxidase-conjugated anti-rabbit IgG antibody (dilution ratio: 1:10,000) as a secondary antibody.

Also, in order to confirm that the amounts of the protein applied were uniform in all the samples, β-actin was detected by allowing anti-β-actin (SC-1616, product of Santa Cruz Biotechnologies, dilution ratio: 1:2,000) and the above secondary antibody to react on the blotting membrane from which the primary and secondary antibodies had been removed.

Results

Figure 3:
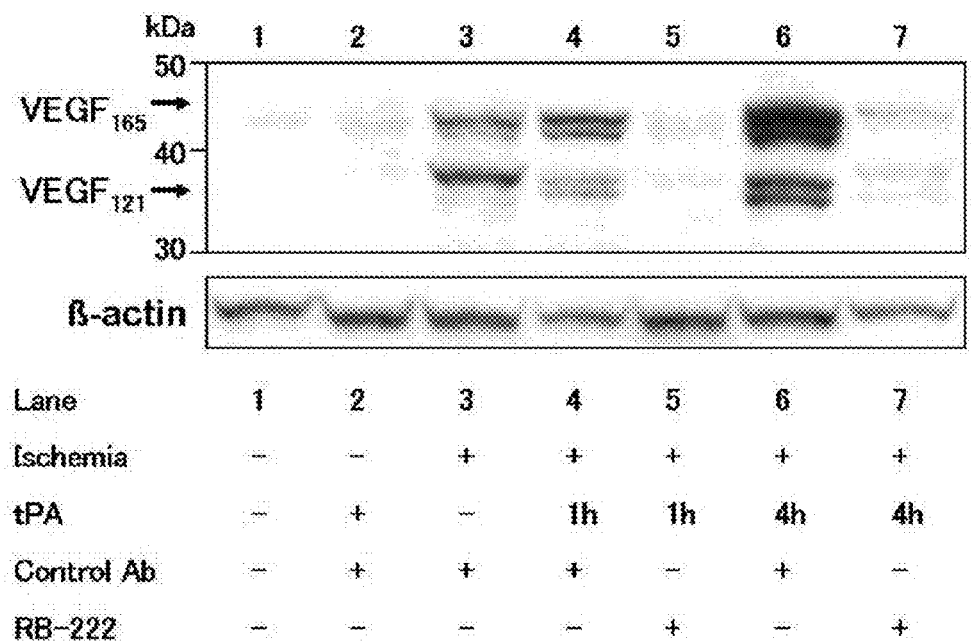
FIG. 3 is a western blot image showing that the expression of VEGF is increased by ischemia and more so at 4 hours after t-PA treatment, but that it is suppressed after combined administration of t-PA and an anti-VEGF antibody (RB-222).

FIG. 3 is a Western blot image showing that the expression of the VEGF is suppressed after administration of the t-PA and the anti-VEGF antibody in combination.

Lane 1 indicates a sample of the animal that was not injected with the thrombus for the onset of cerebral infarction. Lane 2 indicates a sample of the animal that was not injected with the thrombus for the onset of cerebral infarction but received the t-PA and the control antibody. Lane 3 indicates a sample of the animal that received only the control antibody one hour after the onset of cerebral infarction induced by injection of the thrombus. Lane 4 indicates a sample of the animal that received the t-PA and the control antibody one hour after the onset of cerebral infarction induced by injection of the thrombus. Lane 5 indicates a sample of the animal that received the t-PA and the anti-VEGF antibody one hour after the onset of cerebral infarction induced by injection of the thrombus. Lane 6 indicates a sample of the animal that received the t-PA and the control antibody four hours after the onset of cerebral infarction induced by injection of the thrombus. Lane 7 indicates a sample of the animal that received the t-PA and the VEGF antibody in combination four hours after the onset of cerebral infarction induced by injection of the thrombus.

The expression of the VEGF was observed in Lanes 3 and 4. The expression level of the VEGF observed in Lane 6 was found to be very high. In Lanes 1, 2, 5 and 7, almost no expression of the VEGF was observed.

The difference between the VEGF levels detected in the lanes was not correlated with the difference between the β-actin levels detected in the lanes. Through comparison among Lanes 3, 4 and 5, the administration of the t-PA four hours after the onset of cerebral infarction induced by injection of the thrombus was found to considerably increase the expression level of the VEGF. Through comparison between Lanes 4 and 5 and between Lanes 6 and 7, the combined administration of the t-PA and the anti-VEGF antibody was found to considerably suppress the expression of the VEGF.

Ischemic disorders of vascular endothelial cells and the subsequent functional failures of the blood brain barrier are known to be involved with cerebral hemorrhage after administration of t-PA. As is also known, VEGF activates MMP-9 and the activated MMP-9 degrades proteins involved with the blood brain barrier such as zonula occludens-1 and basement membrane type IV collagen. Thus, without being bound by the theory, the action mechanism of the combined administration of the t-PA and the anti-VEGF antibody may be explained as follows. Specifically, the combined administration of the t-PA and the anti-VEGF antibody suppresses an increase in VEGF caused by administration of the t-PA after an acute stage of cerebral infarction to prevent functional failures of the blood brain barrier involving MMP-9 activation, and to prevent cerebral hemorrhage.

Example 3

Evaluation of Effects of Combined Administration of t-PA and anti-VEGF Antibody

The combined administration of the t-PA and the anti-VEGF antibody was performed as described in Example 2. The effects of the combined administration of the t-PA and the anti-VEGF antibody four hours after the onset of cerebral infarction induced by injection of the thrombus were evaluated by measuring the cerebral infarct volume, edema volume, cerebral hemorrhage volume, and motor function scale of the TTC-stained cerebral coronal section prepared 24 hours after the onset of cerebral infarction induced by injection of the thrombus.

The cerebral infarct volume and the edema volume of the TTC-stained cerebral coronal section were calculated according to Swanson, R. A., et al. (*J. Cereb. Blood Flow Metab.* (1990) 10:290-293). The statistical significance was validated by ANOVA (analysis of variance), and post hoc comparisons were performed by the Tukey method.

The cerebral hemorrhage volume was measured using a spectrophotometer as the hemoglobin concentration per 1 dL of the cerebral tissue at the side where the above treatment had been performed (unit: g/dL).

The motor function scale was evaluated based on 5 grades according to Andersen, M., et al. (*Stroke* (1999) 30:1464-1471) (Grade 0: No motor disorder, Grade 1: the forelimb on the opposite side to that where the treatment had been performed was curved, Grade 2: Reduction of resistance to the movement of pushing the body toward the paralysis side, Grade 3: Spontaneous rotation to the paralysis side, and Grade 4: Death). In comparison of the motor function scale, the statistical significance was validated by ANOVA (analysis of variance), and post hoc comparisons were performed by the Tukey method.

Results of Cerebral Infarct Volume, Edema Volume, Cerebral Hemorrhage Volume

Figure 4A:
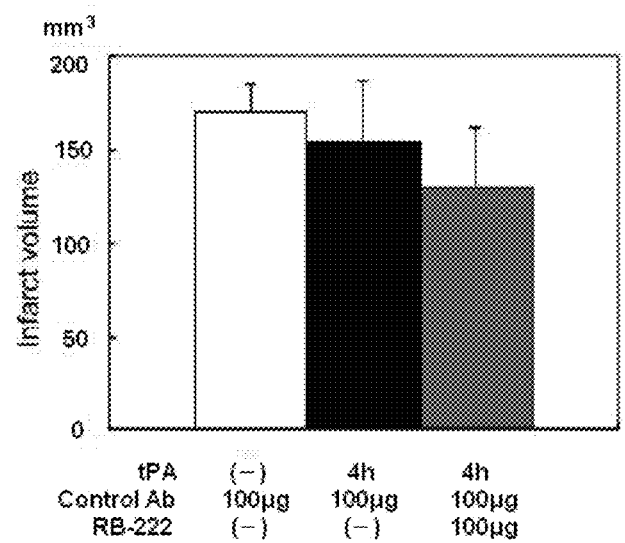
FIG. 4A is a bar graph showing the cerebral infarct volume of a triphenyltetrazolium salt (TTC) stained cerebral coronal section of a rat that received t-PA and an anti-VEGF antibody four hours after the onset of cerebral infarction induced by injection of a thrombus, where the cerebral coronal section is sampled 24 hours after the onset and the vertical axis corresponds to infarct volume ($mm^3$)
Figure 4B:
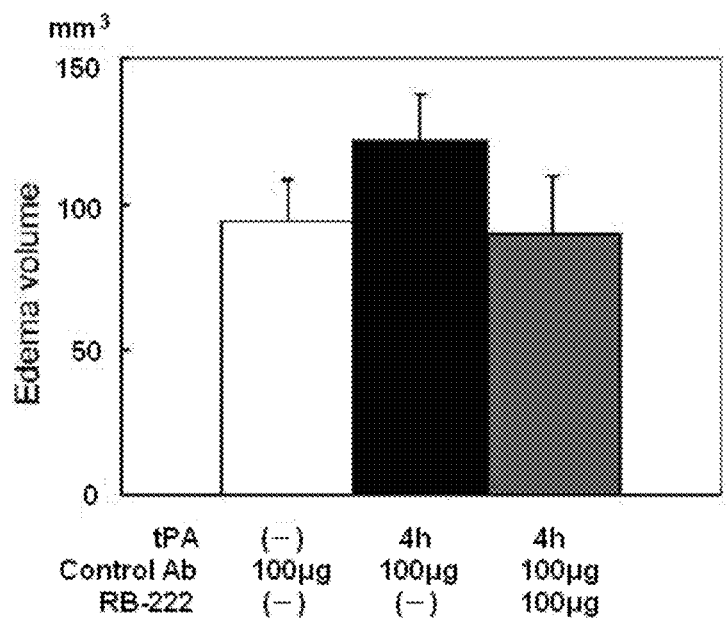
FIG. 4B is a bar graph showing the edema volume of a TTC-stained cerebral coronal section of a rat that received t-PA and an anti-VEGF antibody four hours after the onset of cerebral infarction induced by injection of a thrombus, where the cerebral coronal section is sampled 24 hours after the onset and the vertical axis corresponds to edema volume ($mm^3$)
Figure 4C:
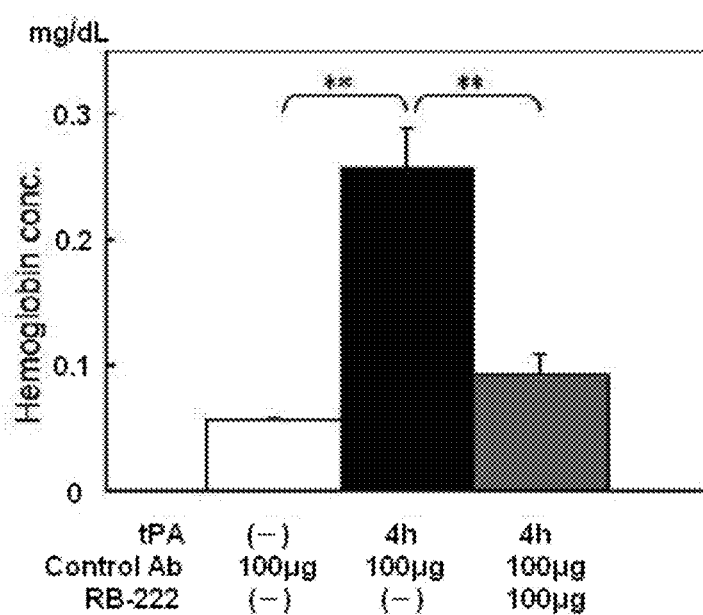
FIG. 4C is a bar graph showing the cerebral hemorrhage volume of a TTC-stained cerebral coronal section of a rat that received t-PA and an anti-VEGF antibody four hours after the onset of cerebral infarction induced by injection of a thrombus, where the cerebral coronal section is sampled 24 hours after the onset and the vertical axis corresponds to the cerebral hemorrhage volume (hemoglobin concentration) (mg/dL).

FIGS. 4A to 4C are bar graphs respectively showing the cerebral infarct volume, edema volume, and cerebral hemorrhage volume of the TTC-stained cerebral coronal section prepared 24 hours after the onset of cerebral infarction induced by injection of the thrombus. The white bar corresponds to a group that received only the control antibody four hours after the onset of cerebral infarction induced by injection of the thrombus. The black bar corresponds to a group that received the t-PA and the control antibody four hours after the onset of cerebral infarction induced by injection of the thrombus. The gray bar corresponds to a group that received the t-PA and the anti-VEGF antibody four hours after the onset of cerebral infarction induced by injection of the thrombus. Each group contained 6 individuals.

From these results, the combined administration of the t-PA and the anti-VEGF antibody could not reduce the cerebral infarct volume and the edema volume but could reduce the cerebral hemorrhage volume, as compared with the group that received the t-PA and the control antibody (P=0.013).

Evaluation Results of Motor Function Scale

Figure 4D:
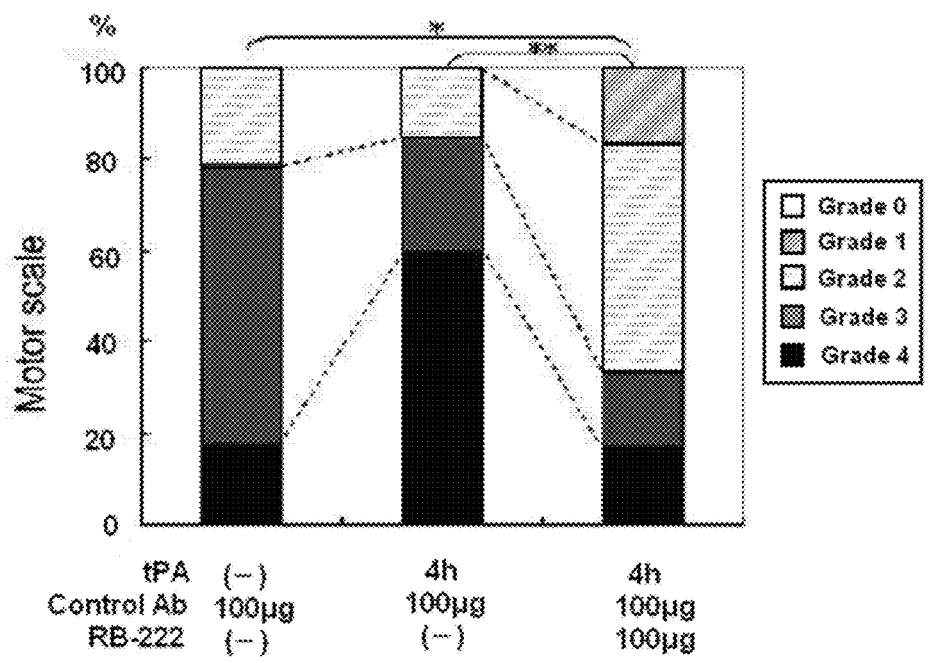
FIG. 4D is a band graph showing the motor function scale of a rat that received t-PA and an anti-VEGF antibody four hours after the onset of cerebral infarction induced by injection of a thrombus, where the motor function scale is evaluated 24 hours after the onset and the vertical axis corresponds to motor scale.

FIG. 4D is a band graph showing motor function scale 24 hours after the onset of cerebral infarction induced by injection of the thrombus. Each color of the bands indicates the number of individuals ranked as each of the 5 grades. The left-hand band corresponds to a group (the number of individuals: 23) that received only the control antibody four hours after the onset of cerebral infarction induced by injection of the thrombus. The center band corresponds to a group (the number of individuals: 20) that received the t-PA and the control antibody four hours after the onset of cerebral infarction induced by injection of the thrombus. The right-hand band corresponds to a group (the number of individuals: 12) that received the t-PA and the anti-VEGF antibody four hours after the onset of cerebral infarction induced by injection of the thrombus.

Through comparison between the left-hand band and the center band, the group that received the t-PA and the control antibody four hours after the onset of cerebral infarction was found to be worse in prognosis than the group that received only the control antibody. From this result, it could be confirmed that the cerebral infarction rat model realizes a state of concomitantly occurring cerebral hemorrhage and cerebral infarction exacerbation accompanied with the administration of the t-PA after an acute stage of cerebral infarction in human.

Through comparison between the center band and the right-hand band, the combined administration of the t-PA and the anti-VEGF antibody showed better prognosis than in the combined administration of the t-PA and the control antibody (P=0.0001). Furthermore, through the left-hand band and the right-hand band, the combined administration of the t-PA and the anti-VEGF antibody showed better prognosis than in the administration of the control antibody alone (P=0.045).

Notably, the rat that had undergone the combined administration of the t-PA and the anti-VEGF antibody was subjected to pathological autopsy, and as a result there was no antigen-antibody complex in the liver, the pancreas or the kidney.

From the above experimental results, it was found that the combined administration of the t-PA and the anti-VEGF antibody can extend the time window for administration of the t-PA in patients with the onset of cerebral infarction, as well as can improve motor functions and survival rates while preventing concomitantly occurring cerebral hemorrhage.

Example 4

Combined Administration of t-PA and SU1498

Whether a VEGF receptor kinase inhibitor can replace the anti-VEGF antibody was investigated as follows.

SU1498 is ((E)-3-(3,5-diisopropyl-4-hydroxylphenyl)-2-((3-phenyl-n-propyl)aminocarbonyl)acrylonitrile, product of Calbiochem, Catalog No. 572888). This was used as an inhibitor specific to the VEGF receptor. SU1498 was dissolved in 1 mL of DMSO (dimethylsulfoxide) so as to attain a concentration of 20 mg/kg (per 1 kg of the body weight of each patient), and the resultant solution was single-bolus administered together with t-PA four hours after the onset of cerebral infarction. For the control experiment, only the solvent DMSO was administered to each patient in an amount of 1 mL per 1 kg of the body weight of the patient.

Evaluation of Effects of Combined Administration of t-PA and SU1498

The effects of the combined administration of t-PA and SU1498 four hours after cerebral infarction were evaluated in the same manner as in Example 3 based on the cerebral infarct volume, edema volume, cerebral hemorrhage volume, and motor function scale of the TTC-stained cerebral coronal section 24 hours after the onset of cerebral infarction induced by injection of the thrombus.

Figure 5A:
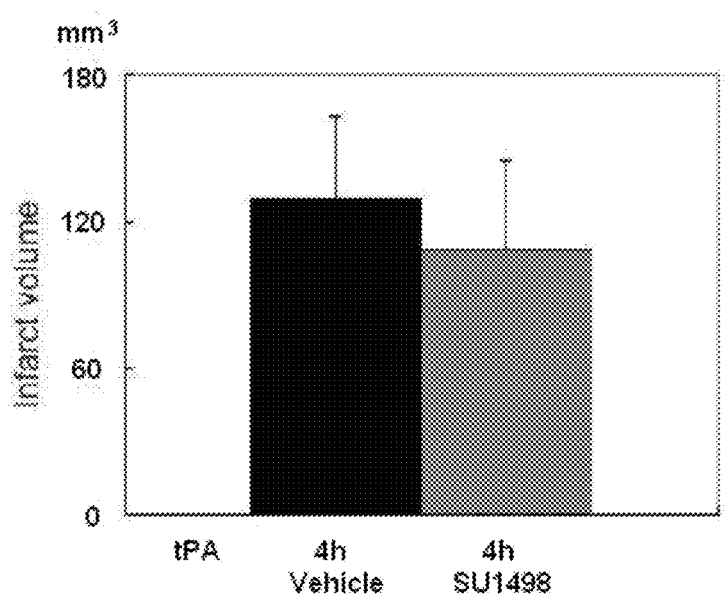
FIG. 5A is a bar graph showing the cerebral infarct volume of a TTC-stained cerebral coronal section of a rat that received t-PA and the VEGF receptor kinase inhibitor SU1498 four hours after the onset of cerebral infarction induced by injection of a thrombus, where the cerebral coronal section is sampled 24 hours after the onset and the vertical axis corresponds to infarct volume ($mm^3$)
Figure 5B:
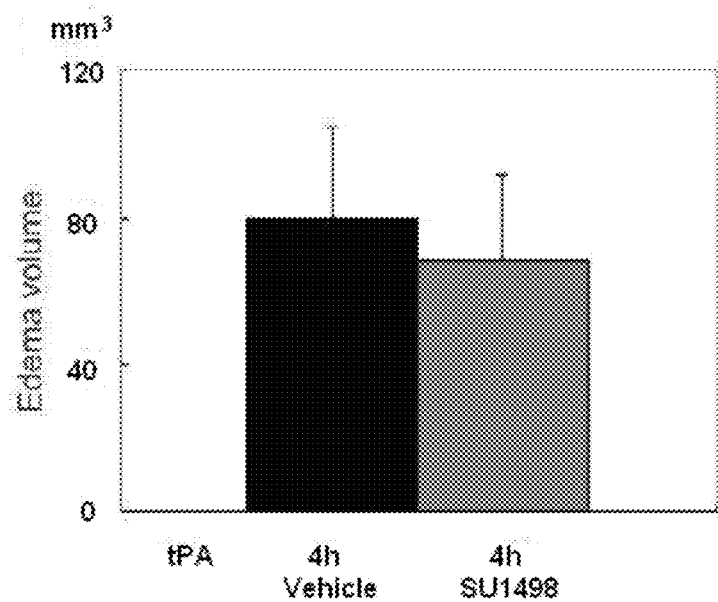
FIG. 5B is a bar graph showing the edema volume of a TTC-stained cerebral coronal section of a rat that received t-PA and SU1498 four hours after the onset of cerebral infarction induced by injection of a thrombus, where the cerebral coronal section is sampled 24 hours after the onset and the vertical axis corresponds to edema volume ($mm^3$)
Figure 5C:
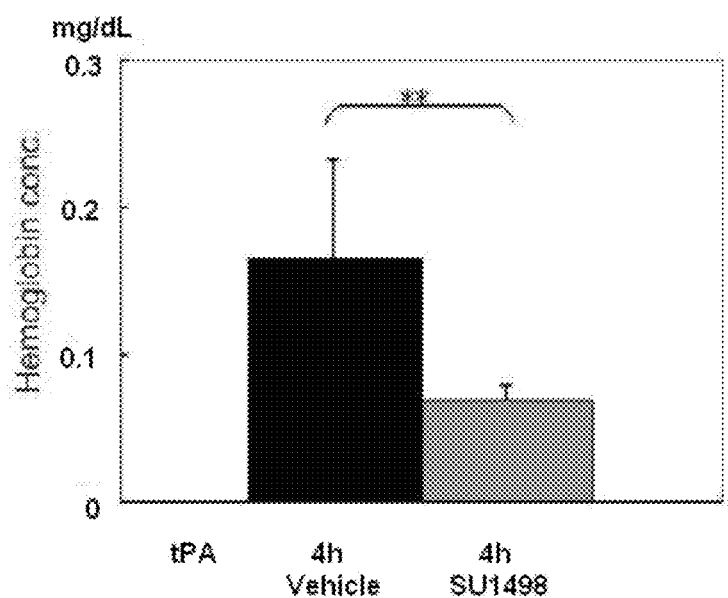
FIG. 5C is a bar graph showing the cerebral hemorrhage volume of a TTC-stained cerebral coronal section of a rat that received t-PA and SU1498 four hours after the onset of cerebral infarction induced by injection of a thrombus, where the cerebral coronal section is sampled 24 hours after the onset and the vertical axis corresponds to the cerebral hemorrhage volume (hemoglobin concentration) (mg/dL).

Results of Cerebral Infarct Volume, Edema Volume, and Cerebral Hemorrhage Volume FIGS. 5A to 5C are bar graphs respectively showing the cerebral infarct volume, edema volume, and cerebral hemorrhage volume of the TTC-stained cerebral coronal section of the rat that received the t-PA and the SU1498 four hours after the onset of cerebral infarction induced by injection of the thrombus, where the cerebral coronal section was sampled 24 hours after the onset. The black bar corresponds to a group that received the t-PA and the DMSO four hours after the onset of cerebral infarction induced by injection of the thrombus. The gray bar corresponds to a group that received the t-PA and the SU1498 four hours after the onset of cerebral infarction induced by injection of the thrombus. Each group contained 6 individuals.

From these results, the combined administration of the t-PA and the SU1498 could not reduce the cerebral infarct volume and edema volume but could reduce the cerebral hemorrhage volume, as compared with the group that received the t-PA and the DMSO (P=0.005).

Evaluation results of Motor Function Scale

Figure 5D:
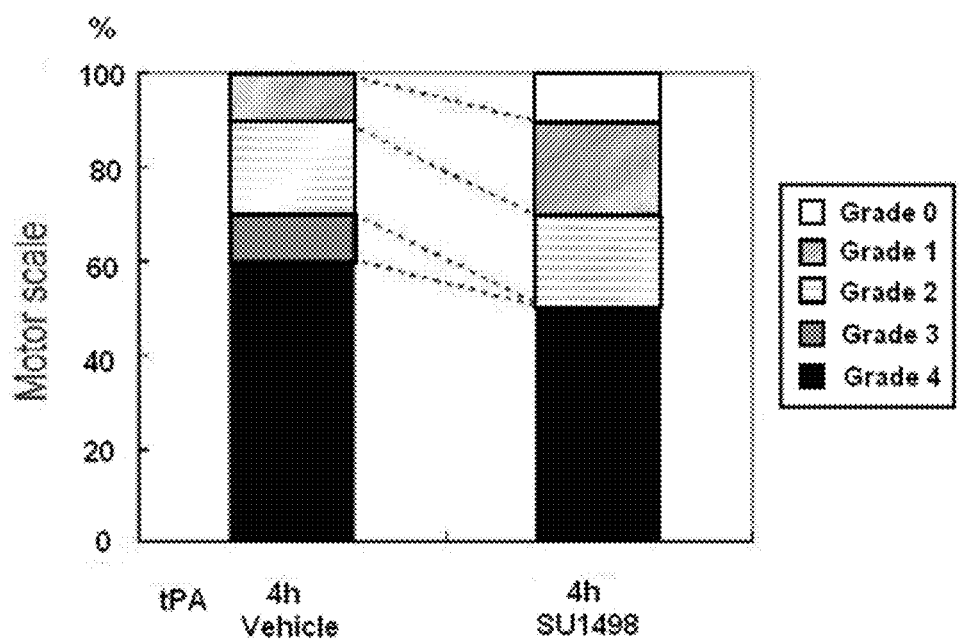
FIG. 5D is a band graph showing the motor function scale of a rat that received t-PA and SU1498 four hours after the onset of cerebral infarction induced by injection of a thrombus, where the motor function scale is evaluated 24 hours after the onset and the vertical axis corresponds to motor scale.

FIG. 5D is a band graph showing motor function scale of the rat that received the t-PA and SU1498 four hours after the onset of cerebral infarction induced by injection of the thrombus, where the motor function scale was measured 24 hours after the onset. The colors of the bands correspond to the 5 grades. The left-hand band corresponds to a group that received the t-PA and the DMSO four hours after the onset of cerebral infarction induced by injection of the thrombus. The right-hand band corresponds to a group that received the t-PA and the SU1498 four hours after the onset of cerebral infarction induced by injection of the thrombus. Each group contained 10 individuals.

Through comparison between the left-hand band and the right-hand band, the group that received the t-PA and the SU1498 four hours after the onset of cerebral infarction was found to be better in prognosis than the group that received the t-PA and the DMSO.

Similar to the combined administration of the t-PA and the anti-VEGF antibody, it was found from the above experimental results that the combined administration of the t-PA and the SU1498 can extend the time window for administration of the t-PA in patients with the onset of cerebral infarction, as well as can improve motor functions and survival rates while preventing concomitantly occurring cerebral hemorrhage.

The pharmaceutical composition may be administered to a patient after an acute stage of ischemic events including cerebral infarction, cardiac infarction, or pulmonary embolism, and can advantageously improve exacerbation of prognosis and complications such as cerebral hemorrhage. Thus, the pharmaceutical composition can suitably be used for the treatment of severe ischemic events including cerebral infarction, cardiac infarction, or pulmonary embolism.

Exemplary embodiments of the present invention are as follows.

1. In one embodiment, a pharmaceutical composition or a treatment method using the composition are provided for treating severe ischemic events including cerebral infarction, cardiac infarction, or pulmonary embolism. The composition contains a thrombolytic agent, and at least one inhibitor of VEGF R-mediated signal transduction. For example, the inhibitor inhibits the binding of VEGF to VEGF receptor to inhibit VEGF R-mediated signal transduction.

2. The composition or method of 1. wherein the inhibitor decreases the binding of VEGF to VEGF-R.

3. The composition or method of 2. wherein the inhibitor is a specific binding partner for VEGF or for VEGF-R.

4. The composition or method of 3. wherein the specific binding partner is an antibody, an aptamer, or a VEGF peptide or small molecule mimic that binds to VEGF-R but does not activate it, or a VEGF-R peptide or small molecule mimic that reduces the effective level of VEGF available for stimulating the VEGF-R.

5. The composition or method of 4. wherein the inhibitor is an antibody that binds VEGF-R and antagonizes said receptor or an antibody that binds VEGF and causes it to be eliminated from the blood.

6. In one embodiment, the composition or method of 1. wherein the inhibitor inhibits the release of VEGF from platelets.

7. The composition or method of 6. wherein the inhibitor decreases the binding of ADP to its receptor.

8. The composition or method of 7. wherein the inhibitor is a specific binding partner for ADP or for a receptor for ADP.

9. The composition or method of 8. wherein the specific binding partner is an antibody, an aptamer, or an ADP peptide or small molecule mimic that binds to a receptor for ADP but does not activate it, or an ADP receptor peptide or small molecule mimic that adsorbs ADP.

10. In one embodiment, the composition or method of 1. wherein the inhibitor interacts with a component of the VEGF-R signaling pathway or with an enzyme that modifies a component of the VEGF-R signaling pathway.

11. The composition or method of 10. wherein the inhibitor inhibits tyrosine kinase or is a tyrosine phosphatase agonist.

12. The composition or method of 1. wherein the inhibitor decreases the production of VEGF or VEGF-R.

13. The composition or method of any one of 10. to 12. wherein the inhibitor is an antisense nucleic acid, a small interfering RNA or a ribozyme.

14. In one embodiment, the composition or method of 1. wherein the inhibitor is coupled to the thrombolytic agent.

15. The composition or method of 14. wherein the inhibitor is coupled to the thrombolytic agent as a fusion protein.

16. The composition or method of 1. wherein the thrombolytic agent is urokinase, streptokinase, tissue plasminogen activator (t-PA) or an analog thereof.

17. The composition or method of any one of 1. to 5. wherein the VEGF-R is VEGF-R2.

18. The composition or method of any one of 1. to 17. wherein said composition is administered after an acute stage of cerebral infarction or other ischemic event.

19. The composition or method of 18. wherein said acute stage is 3 hours to 6 hours of onset of said ischemic event.

20. The composition or method of 18. wherein said acute stage is within 3 hours of onset of said cerebral infarction.

21. The composition or method of any one of 2. to 5. wherein the specific binding partner is selected from the group consisting of: a polyclonal or monoclonal antibody having an activity of inhibiting signal transduction of the VEGF by binding specifically to the VEGF or the VEGF receptor; an antigen-binding fragment of the antibody; a recombinant or chimeric antibody containing the antigen-binding fragment; and a derivative thereof.

22. In one embodiment, the composition or method of any one of 3. to 5. wherein the specific binding partner binds to at least one of VEGF-A and VEGF-A receptor to inhibit signal transduction mediated by the VEGF-A receptor.

23. In one embodiment, the composition or method of 22., the specific binding partner is an anti-VEGF-A neutralizing antibody or a derivative thereof.

24. The composition or method of any one of 7. to 9., wherein the specific binding partner is selected from the group consisting of: a polyclonal or monoclonal antibody having an activity of inhibiting signal transduction of the ADP by binding specifically to the ADP or the ADP receptor; an antigen-binding fragment of the antibody; a recombinant or chimeric antibody containing the antigen-binding fragment; and a derivative thereof.

25. The composition or method of 10. or 11., wherein the inhibitor is (E)-3-(3,5-diisopropyl-4-hydroxyphenyl)-2-((3-phenyl-n-propyl)amino-carbonyl)acrylonitrile).

26. A kit containing: a thrombolytic agent; and an inhibitor of VEGF R-mediated signal transduction.

The invention claimed is:

1. A method to suppress or reduce concomitantly occurring cerebral hemorrhage and cerebral infarction exacerbation that accompany the administration of a plasminogen activator after an acute stage of ischemic cerebral infarction in a human subject comprising administering to said subject a combination of a plasminogen activator and,
   a tyrosine kinase inhibitor that inhibits human VEGF-R2 response to VEGF,
   wherein administration of said combination extends the time window for administration of said plasminogen activator to said human subject after the onset of cerebral infarction beyond that for administration of said plasminogen activator alone, and
   wherein administration of said combination suppresses or reduces said concomitantly occurring cerebral hemorrhage and cerebral infarction exacerbation; and
   wherein the administration of said combination is between 3-6 hours of the onset of said cerebral infarction, and
   wherein the plasminogen activator and the inhibitor are administered in the same composition or administered separately; and
   within the tyrosine kinase inhibitor that inhibits human VEGF-R2 response to VEGF is selected from the group consisting of SU1498, SU5416, cediranib (AZD2171), sunitinib (SU11248), vatalanib (PTK787/ZK222584), sorafenib, and pazopanib (GW786034B).

2. The method of claim 1 wherein the plasminogen activator and the inhibitor are administered in the same composition.

3. The method of claim 1 wherein the plasminogen activator is tissue plasminogen activator (tPA), streptokinase, urokinase or desmoteplase.

4. The method of claim 1 wherein the tyrosine kinase inhibitor is SU1498.

* * * * *